US00PP20781P2

(12) United States Plant Patent
Sahin-Georgiadou

(10) Patent No.: US PP20,781 P2
(45) Date of Patent: Feb. 23, 2010

(54) ***CENTAUREA* PLANT NAMED 'AMETHYST DREAM'**

(50) Latin Name: *Centaurea montana*
Varietal Denomination: Amethyst Dream

(75) Inventor: Elisabeth Sahin-Georgiadou, Alphen aan den Rijn (NL)

(73) Assignee: K. Sahin Zaden B.V., Alphen aan den Rijn (NL)

( * ) Notice: Subject to any disclaimer, the term of this patent is extended or adjusted under 35 U.S.C. 154(b) by 0 days.

(21) Appl. No.: 12/290,125

(22) Filed: Oct. 28, 2008

(51) Int. Cl.
*A01H 5/00* (2006.01)

(52) U.S. Cl. ..... Plt./263.1

(58) Field of Classification Search ..... Plt./263, Plt./263.1
See application file for complete search history.

*Primary Examiner*—Susan B McCormick Ewoldt
(74) *Attorney, Agent, or Firm*—C. A. Whealy

(57) ABSTRACT

A new and distinct cultivar of *Centaurea* plant named 'Amethyst Dream', characterized by its upright and mounding plant habit; vigorous growth habit; large inflorescences with dark purple-colored ray and disc florets; and good garden performance.

1 Drawing Sheet

Botanical designation: *Centaurea montana.*
Cultivar denomination: 'Amethyst Dream'.

BACKGROUND OF THE INVENTION

The present invention relates to a new and distinct cultivar of *Centaurea* plant, botanically known as *Centaurea montana,* and hereinafter referred to by the name 'Amethyst Dream'.

The new *Centaurea* plant is a naturally-occurring whole plant mutation of an unnamed selection of *Centaurea montana,* not patented. The new *Centaurea* plant was discovered and selected by the Inventor as a single flowering plant within a population of plants of the unnamed selection in 2002 in a controlled outdoor nursery environment in Alphen aan den Rijn, The Netherlands. The selection of this plant was based on its unique inflorescence coloration.

Asexual reproduction of the new *Centaurea* plant by vegetative cuttings in a controlled environment in Lancaster, Pa. since October, 2003, has shown that the unique features of this new *Centaurea* plant are stable and reproduced true to type in successive generations.

SUMMARY OF THE INVENTION

Plants of the new *Centaurea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Amethyst Dream'. These characteristics in combination distinguish 'Amethyst Dream' as a new and distinct cultivar of *Centaurea:*

1. Upright and mounding plant habit.
2. Strong and vigorous growth habit.
3. Large inflorescences with dark purple-colored ray and disc florets.
4. Good garden performance.

In side-by-side comparisons conducted in Lancaster, Pa., plants of the new *Centaurea* differed from plants of the parent selection primarily in inflorescence coloration as plants of the parent selection have red violet-colored ray and disc florets.

Plants of the new *Centaurea* can be compared to plants of *Centaurea montana* 'Amethyst in Snow', disclosed in U.S. Plant Pat. No. 18,284. In side-by-side comparisons conducted in Lancaster, Pa., plants of the new *Centaurea* differed from plants of 'Amethyst in Snow' primarily in inflorescence coloration. In addition, plants of the new *Centaurea* were more upright than and not as outwardly spreading as plants of 'Amethyst in Snow'.

BRIEF DESCRIPTION OF THE PHOTOGRAPHS

The accompanying photographs illustrate the overall appearance of the new *Centaurea.* These photographs show the colors as true as it is reasonably possible to obtain in colored reproductions of this type. Colors in the photographs may differ slightly from the color values cited in the detailed botanical description which accurately describe the colors of the new *Centaurea.*

The photograph at the bottom of the sheet comprises a side perspective view of a typical flowering plant of 'Amethyst Dream' grown in a container.

The photograph at the top of the sheet is a close-up view of a typical inflorescence of 'Amethyst Dream'.

DETAILED BOTANICAL DESCRIPTION

Plants used for the aforementioned photographs and following observations and measurements describe plants grown in Lancaster, Pa. during the spring in one-gallon containers in a polyethylene-covered greenhouse and under conditions and practices which approximate those generally used in commercial *Centaurea* production. During the production of the plants, day temperatures averaged 21° C. and night temperatures averaged 2° C. Measurements and numerical values represent averages for typical four-month old flowering plants. In the following description, color references are made to The Royal Horticultural Society Colour Chart, 1995 Edition, except where general terms of ordinary dictionary significance are used.

Botanical classification: *Centaurea montana* 'Amethyst Dream'.

Parentage: Naturally-occurring whole plant mutation of an unnamed selection of *Centaurea montana,* not patented.

Propagation:

*Type.*—Terminal vegetative cuttings.

*Time to initiate roots.*—About six days at 29° C.

*Time to produce a rooted cutting, summer.*—About 14 days at 29° C.

*Time to produce a rooted cutting, winter.*—About 18 days at 20° C.

*Root description.*—Medium in thickness; white in color.

*Rooting habit.*—Freely branching; moderately dense.

Plant description:

*Plant form/growth habit.*—Upright and mounding plant habit. Strong and vigorous growth habit.

*Plant height.*—About 20 cm.

*Plant diameter or spread.*—About 29 cm.

*Lateral branches.*—Quantity per plant: Freely branching habit with about 18 basal branches developing per plant. Length: About 22 cm. Diameter: About 5 mm. Internode length: About 2.7 cm. Aspect: Upright to somewhat outwardly spreading. Strength: Strong. Texture: Tomentose. Color: Close to 147B.

Foliage description:

*Arrangement.*—Alternate, simple; sessile.

*Length.*—About 8.4 cm.

*Width.*—About 2.4 cm.

*Shape.*—Oblanceolate.

*Apex.*—Acute.

*Base.*—Decurrent.

*Margin.*—Entire.

*Texture, upper and lower surfaces.*—Tomentose.

*Venation pattern.*—Pinnate, arcuate.

*Color.*—Developing leaves, upper surface: Close to 147C. Developing leaves, lower surface: Close to 148C. Fully expanded leaves, upper surface: Close to 147A to 147B; venation, close to 146D. Fully expanded leaves, lower surface: Close to 148B; venation, close to 147C.

Inflorescence description:

*Appearance.*—Rotate composite inflorescence form; inflorescences typically terminal with one inflorescence per terminal. Inflorescences positioned above the foliage. Inflorescences face mostly upright. Inflorescences not fragrant.

*Time to flower.*—Under natural season conditions, plants flower begin to flower in the late spring and continue to flower throughout the early summer.

*Post-production longevity.*—Inflorescences maintain good substance for about seven to ten days on the plant; inflorescences persistent.

*Inflorescence bud.*—Height: About 2.4 cm. Diameter: About 1.1 cm. Shape: Ovoid. Color: Close to 93A.

*Inflorescence size.*—Diameter: About 7.4 cm. Depth (height): About 4.5 cm. Disc diameter: About 3.3 cm. Receptacle diameter: About 1.2 cm. Receptacle height: About 1.7 cm.

*Ray florets.*—Shape: Lanceolate; tubular at the base, flaring towards the apex into about six fringed and narrow linear segments that curved upwardly. Length: About 5 cm. Corolla tube length: About 2.7 cm. Width, base: About 1 mm. Width, apex: About 1.3 cm to 1.6 cm. Margin: Entire. Texture, upper surface: Smooth, glabrous; satiny. Texture, lower surface: Sparsely pubescent. Number of ray florets per inflorescence: About 20 in a single whorl. Color: When opening, upper surface: Close to 83A. When opening, lower surface: Close to 83B to 83C; towards the base, close to 155D. Fully opened, upper surface: Close to 83B. Fully opened, lower surface: Close to 83C.

*Disc florets.*—Arrangement: Massed in the center of the receptacle. Shape: Tubular; apex flaring into five linear segments. Length: About 2.5 cm. Diameter, base: About 1 mm. Diameter, apex: About 6 mm. Number of disc florets per inflorescence: About 50. Color, immature: Apex: Close to 93A. Mid-section: Close to 83A; towards the base, close to 86D. Base: Close to 155D. Color, mature: Apex: Close to 86A. Mid-section: Close to 86B to 86C; towards the base, close to 86D. Base: Close to 155D.

*Phyllaries.*—Quantity per inflorescence: About 34 in about seven to eight whorls. Length: About 1.2 cm. Width: About 5 mm. Shape: Ovate. Apex: Acute to lacerate. Base: Truncate, fused. Margin: Fringed, ragged or lacerate. Texture, upper and lower surfaces: Smooth; glabrous. Color, upper surface: Close to 148A. Color, lower surface: Close to 147C; towards the margins, close to 200B.

*Peduncles.*—Length: About 7 cm. Diameter: About 3.5 mm. Strength: Strong. Aspect: Mostly upright to about 45° from vertical. Texture: Pubescent. Color: Close to 147B.

*Reproductive organs* (*present on disc florets only*).—Androecium: Quantity of stamens per disc floret: About five. Filament length: About 1.3 cm. Filament color: Close to 85D. Anther shape: Narrowly oblong. Anther length: About 7 mm. Anther color: Close to 79D. Pollen amount: Moderate. Pollen color: Close to 198A. Gynoecium: Quantity of pistils per disc floret: One. Pistil length: About 2.8 cm. Stigma shape: Biparted. Stigma color: Close to 83A. Style length: About 2.5 cm. Style color: Close to 83B. Ovary color: Close to 157B.

*Seed/fruit.*—Seed and fruit production has not been observed.

Disease/pest resistance: Plants of the new *Centaurea* have not been shown to be resistant to pathogens and pests common to *Centaurea.*

Garden performance: Plants of the new *Centaurea* have been observed to have good garden performance and tolerate wind, rain and temperatures ranging from about −20° C. to about 40° C.

It is claimed:

1. A new and distinct *Centaurea* plant named 'Amethyst Dream' as illustrated and described.

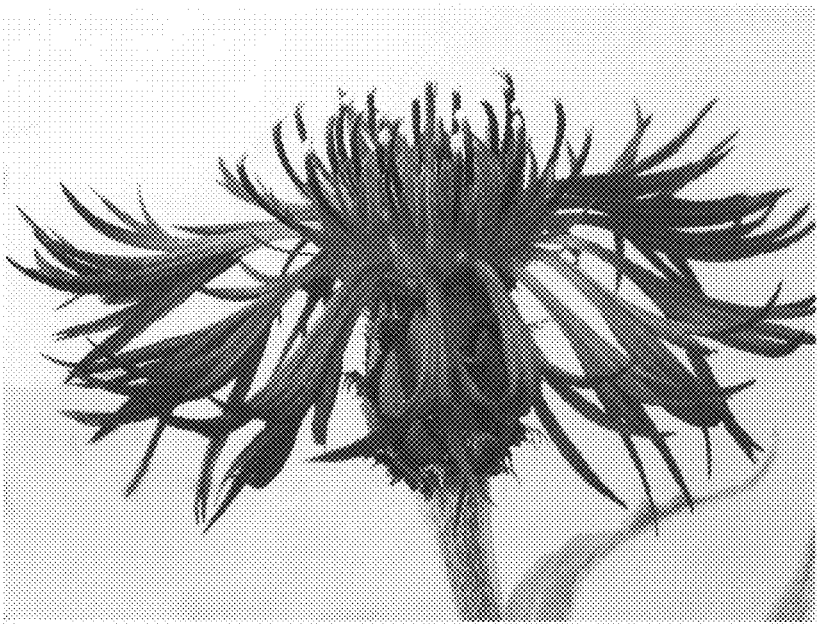
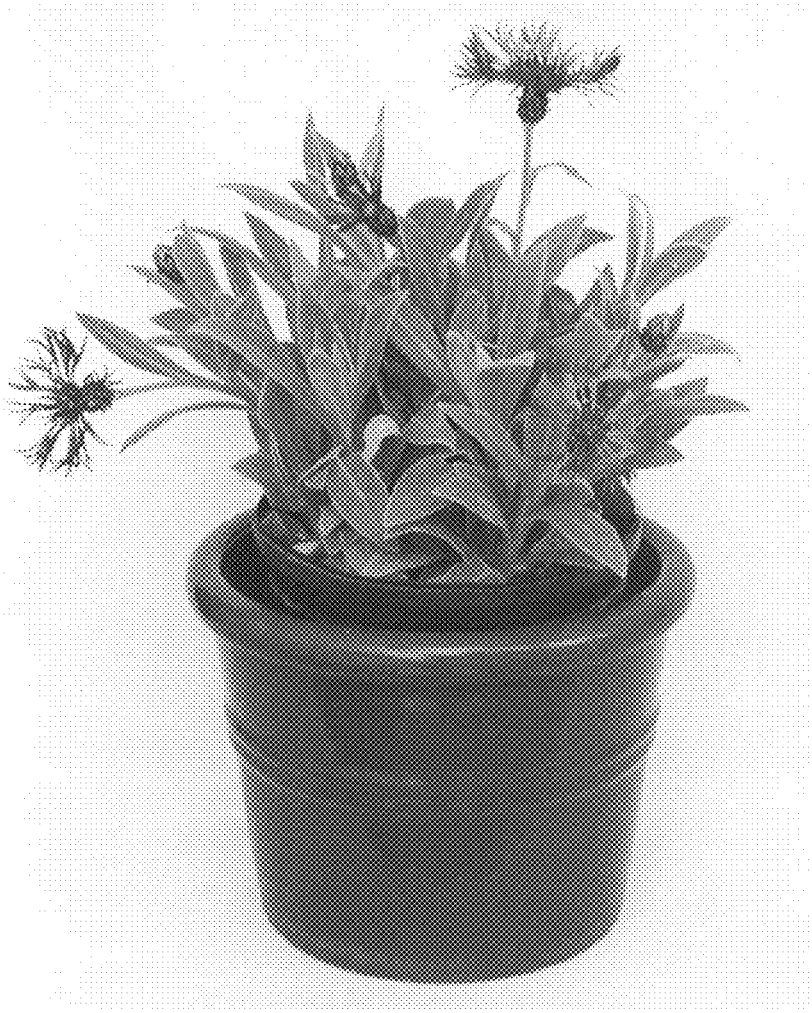

* * * * *